(12) United States Patent
Koyama et al.

(10) Patent No.: US 6,210,912 B1
(45) Date of Patent: Apr. 3, 2001

(54) METHOD FOR EXAMINING CHRONIC REJECTION REACTIONS FOLLOWING ORGAN TRANSPLANTATION AND METHOD FOR DETERMINING URINE COMPONENTS

(75) Inventors: Isamu Koyama, Tokyo; Tadaki Yasumura, Shiga; Kyuichi Nemoto, Tochigi; Takako Mae; Kan Saiga, both of Tokyo; Hisako Takagi, Gunma; Atsuko Isoda, Gunma; Toshio Tanabe, Gunma, all of (JP)

(73) Assignee: Nippon Kayaku Kabushiki Kaisha, Tokyo (JP)

( * ) Notice: Subject to any disclaimer, the term of this patent is extended or adjusted under 35 U.S.C. 154(b) by 0 days.

(21) Appl. No.: 09/230,398

(22) PCT Filed: Jul. 29, 1997

(86) PCT No.: PCT/JP97/02627

§ 371 Date: Feb. 12, 1999

§ 102(e) Date: Feb. 12, 1999

(87) PCT Pub. No.: WO98/05970

PCT Pub. Date: Feb. 12, 1998

(30) Foreign Application Priority Data

Aug. 1, 1996 (JP) .................................................. 8-218151
Oct. 16, 1996 (JP) .................................................. 8-293183
Jun. 17, 1997 (JP) .................................................. 9-175165

(51) Int. Cl.$^7$ ........................ G01N 33/22; G01N 33/573; G01N 33/53; G01N 33/574
(52) U.S. Cl. ............................ 435/7.4; 435/7.1; 435/7.9; 435/7.94; 435/23; 436/116
(58) Field of Search .................................. 435/4, 7.1, 7.4, 435/7.9, 23, 7.94; 436/116

(56) References Cited

FOREIGN PATENT DOCUMENTS 4-183397  6/1992  (JP).
7-159402  6/1995  (JP).

OTHER PUBLICATIONS

Lewis et al. Circulation 93 (4):720–729, Feb. 1996.*
Langrehr et al. Nitrate and Nitrate Production following Orthotopic Liver Transplantation, Portland Press Proc. 8 (Biology of Nitric Oxide, 3) 527–530, 1994.*
Langhrehr et al. Journal of Clinical Investigation, 90 (2): 679–83, 1992.*
Langhrehr et al. Surgery, 112:395–402, 1992.*
J.M. Langrehr, 'Detection of Nitric Oxide by Electron Paramagnetic Resonance Spectroscopy during Rejection and Graft–Versus–Host Disease after Small–Bowel Transplantation in the Rat', Surgery, vol. 1122, No. 2, (1992), pp. 395–402.
Samuel A. Yousem, MD et al.; 'Architectural Remodeling of Lung Allografts in Acute and Chronic Rejection'; Arch Pathol Lab Med–vol. 116, Nov. 1992 pp. 1175 to 1180.
L.A. MacMillan–Crow, et al. 'Nitration and inactivation of manganese superoxide dismutase in chronic rejection of human renal allografts'; Proc. Natl. Acad. Sci. USA–vol. 93, pp. 11853–11858, Oct. 1996 Medical Sciences.

* cited by examiner

*Primary Examiner*—David Saunders
*Assistant Examiner*—Amy DeCloux
(74) *Attorney, Agent, or Firm*—Nields & Lemack

(57) ABSTRACT

A method for detecting the onset of chronic rejection at an early stage after organ transplantation, characterized by assaying nitrogen trioxide ($NO_3$), matrix metalloproteinase (MMP)-2 or the precursor thereof in body fluids drawn out of body.

11 Claims, 2 Drawing Sheets

METHOD FOR EXAMINING CHRONIC REJECTION REACTIONS FOLLOWING ORGAN TRANSPLANTATION AND METHOD FOR DETERMINING URINE COMPONENTS

This application is a national stage filing under 35 U.S.C. §371 from PCT/JP97/02627, filed Jul. 29, 1997.

TECHNICAL FIELD

The present invention relates to methods for detecting the onset of chronic rejection after organ transplantation by examining body fluids drawn out of body, and more specifically, the present invention relates to methods for detecting rejection (chronic rejection) emerging at the chronic stage after organ transplantation by assaying nitrogen trioxide ($NO_3$), matrix metalloproteinase-2 (referred to as "MMP-2") or the precursor thereof in body fluids, and a method for assaying MMP-2 or the precursor thereof in urine.

BACKGROUND OF THE INVENTION

In patients with kidney transplantation, generally, chronic rejection is diagnosed by renal biopsy. However, the patients are suffered from periodic renal biopsy, which may deteriorate the renal function concomitantly. Furthermore, such chronic rejection proceeds slowly, with the resultant poor subjective symptoms, and therefore, most patients reject painful renal biopsy.

Meanwhile, renal function tests giving the indicators of the progress of chronic rejection have been practiced because renal function is damaged due to chronic rejection. At the tests, urine protein, urine albumin, and urine transferrin etc. have been assayed as the indicators of the acceleration of protein permeability, reflecting glomerular abnormality, and blood creatine, blood urea nitrogen (BUN), blood $\beta_2$-microglobulin and blood $\alpha_1$-microglobulin have been assayed as the indicators of the decrease of glomerular filtration rate (GFR). However, the change of the test values in the progress of chronic rejection is mild, and when abnormal test values are detected, the chronic rejection has already exerted symptoms at the end stage. So far, not any test method has been known, which can enable early detection of chronic rejection by assaying endogenous substances in body fluids such as urine and blood. Since no such simple test method is currently present, patients with poor subjective symptoms of chronic rejection fall into the end stage, with no appropriate treatment, so that the patients frequently lose their renal function.

It is an object of the present invention to provide simple methods capable of detecting chronic rejection at its early stage after organ transplantation.

DISCLOSURE OF THE INVENTION $NO_3$ and $NO_2$ are final metabolites of NO radical in biological organisms. No radical is generated from granulocytes and macrophages and the like during inflammation and organ damage Therefore, these metabolites are clinically detected during inflammation, ischemic cardiac diseases due to organ damage, shock, acute rejection after transplantation, and bacterial infection. However, no report about NO radical during chronic rejection after transplantation has been issued. Thus, whether or not NO, is generated in body due to rejection which progresses chronically, and whether or not NO, in body fluids possibly serves as a marker at tests of chronic rejection have been examined, so that it has been found that $NO_3$ in body fluids can serve as a marker at the detection of chronic rejection.

Furthermore, MMP-2, an enzyme degrading collagen composing the basal membrane, works during restoration and regeneration of tissues. For cancers, still furthermore, the enzyme is considered to work to decompose collagen during the infiltration of cancer cells into the basal membrane. After intensive investigations, the inventors have found that MMP-2 or the precursor thereof never leaks, or only a trace amount of them leaks even if it does leak, into body fluids such as urine in normal subjects or patients with no onset of chronic rejection after kidney transplantation, while the amount of MMP-2 or the precursor in the body fluids such as urine in patients with chronic rejection after organ transplantation markedly increases. In accordance with the present invention, it is provided methods for detecting rejection after organ transplantation by assaying endogenous substances such as $NO_3$ and MMP-2 or the precursor in body fluids such as blood and urine, based on the finding that the concentrations of these endogenous substances secreted into body fluids such as blood and urine are significantly increased, following the onset of chronic rejection after organ transplantation; a testing kit for use according to the method; and a method for assaying MMP-2 or the precursor in urine.

More specifically, the present invention relates to (1) a method for detecting the onset of chronic rejection at an early stage after organ transplantation, by examining body fluids drawn out of body;

(2) a method for detecting chronic rejection after organ transplantation, characterized by detecting $NO_3$, MMP-2 or the precursor thereof in body fluids;

(3) the method described above in (2), characterized by detecting $NO_3$ in body fluids;

(4) the method described above in (2), characterized by detecting MMP-2 or the precursor thereof in body fluids;

(5) the method described above in (2), (3) or (4), wherein the body fluids comprise human urine or blood.

(6) the method described above in (2), characterized by detecting MMP-2 or the precursor thereof in an urine sample;

(7) the method described above in (2), (3), (4), (5) or (6), wherein the organ transplantation is kidney transplantation;

(8) the method described above in (6), characterized by presetting a cut-off value for determining the presence or absence of chronic rejection after kidney transplantation within a range of 0.1 to 10.0 ng/ml as the concentration of the MMP-2 precursor in an urine sample;

(9) the method described above in (8), characterized by presetting the cut-off value within a range of 0.5 to 5.0 ng/ml;

(10) the method described above in (6), characterized by assaying the MMP-2 precursor concentration and creatine concentration in an urine sample, and presetting a cut-off value of an index after correction on a creatine concentration basis for determining the presence or absence of chronic rejection after kidney transplantation within a range of 0.1 to 20.0 μg/g·creatine;

(11) the method described above in (10), characterized by presetting the cut-off value within a range of 0.5 to 10.0 μg/g·creatine;

(12) the method described in any of (2) and (4) through (11), wherein the detection is carried out by immunoassay;

(13) the method described above in (12), wherein the immunoassay is enzyme immunoassay;

(14) the method described above in (12) or (13), wherein the immunoassay is sandwich assay;

(15) a method for assaying urine MMP-2 or the precursor thereof by immunoassay;

(16) a kit for detecting the onset of chronic rejection at an early stage after organ transplantation, by examining body fluids drawn out of body;

(17) a kit for detecting the onset of chronic rejection after organ transplantation, y by detecting nitrogen trioxide ($NO_3$), or matrix metalloproteinase (MMP)-2 or the precursor thereof in body fluids;

(18) a kit for detecting the onset of chronic rejection after organ transplantation, by detecting MMP-2 or the precursor thereof in urine or blood;

(19) the kit described above in (18), wherein the detection is carried out by immunoassay;

(20) a method for diagnosing chronic rejection at an early stage after organ transplantation, by examining body fluids;

(21) a diagnostic method of chronic rejection after organ transplantation, characterized by detecting nitrogen trioxide ($NO_3$) or matrix metalloproteinase (MMP)-2 or the precursor thereof in body fluids; and

(22) the diagnostic method described above in (21), wherein the body fluids comprise urine or blood.

BEST MODE FOR CARRYING OUT THE INVENTION

Figure 1:
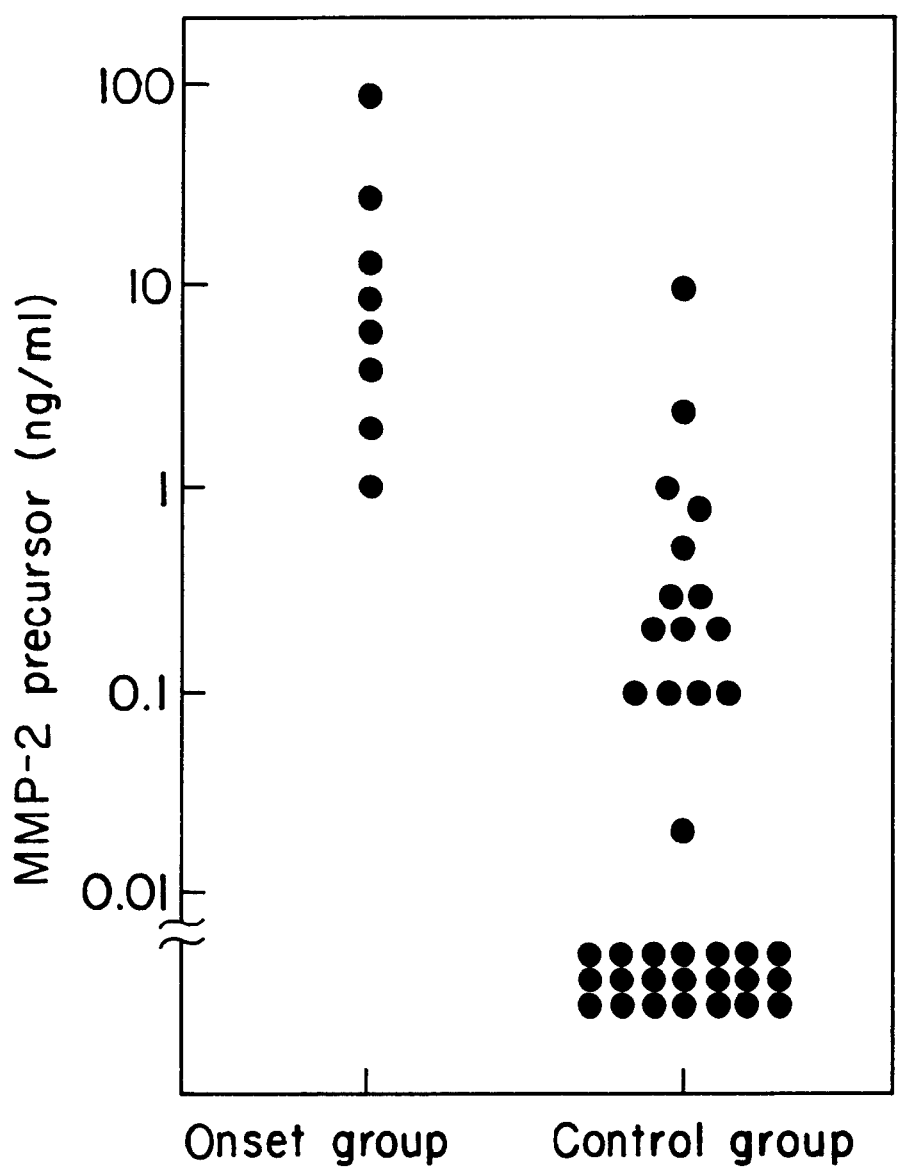
FIG. 1 depicts a histogram of urine MMP-2 precursor concentrations in patients with kidney transplantation.

In accordance with the present invention, it is provided a method for assaying chronic rejection at its early stage after organ transplantation in a simple manner, by assaying endogenous substances specifically secreted in body fluids due to chronic rejection after organ transplantation. In accordance with the present invention, body fluids (samples) include body fluids from human and the like, such as urine and blood components including serum and plasma. Any urine sample may be satisfactory, if the sample is collected or the sample is collected and stored, so that substances to be detected, such as MMP-2 or the precursor might be stable. The timing and method for collecting urine samples are with no specific limitation, as long as they will not damage the clinical meaning of MMP-2 or the precursor or the like. Any urine sample collected and stored in a routine manner may be used. Urine may sometimes be collected in a container with addition of for example antibacterial agents so as to maintain the stability during urine storage, and such urine sample can also be used as long as the antibacterial agents added will not have any interference over the assay. Additionally, the organ transplantation includes kidney transplantation, liver transplantation, cardiac transplantation, and pancreas transplantation, with no specific limitation, but the case of kidney transplantation is particularly preferable.

Endogenous substances include nitrogen trioxide ($NO_3$), matrix metalloproteinase (MMP)-2 or the precursor thereof etc.

The method for assaying (quantitative determination etc.) the amount of $NO_3$ in a sample is known (for example, Griess method), and in accordance with the present invention, the amount of $NO_3$ may be assayed by known methods. For example, $NO_3$ can be determined by high performance liquid chromatography (HPLC) by using a commercially available automatic analyzer of nitrate-form nitrogen and nitrite-form nitrogen. $NO_3$ may also be assayed in a 96-well microplate with commercially available NO calorimetric kits and NO fluorescence assay kits by using a microplate reader and the like. Besides, any system capable of determining $NO_3$ may also be used.

$NO_3$ is present in the sera and the like from normal subjects or patients with organ transplantation but with no onset of chronic rejection, but the amount of $NO_3$ present in the sera and the like from patients with chronic rejection after organ transplantation is significantly increased. By presetting a cut-off value at an appropriate value, therefore, whether or not chronic rejection occurs in these patients can be determined at a high precision. The cut-off value varies, depending on the type of a sample to be used or the type of a transplanted organ. The cut-off value should appropriately be determined, depending on the types, but for a serum sample from a patient with kidney transplantation, preferably, the cut-off value is preset within a range of 50 to 120 $\mu$M ($NO_3$ concentration in the serum).

MMP-2 is released from cells in the form of the precursor, pro-MMP-2. And then the precursor is converted into MMP-2. In accordance with the present invention, the term "precursor of MMP-2" means a substance that may potentially turn into MMP-2, specifically meaning pro-MMP-2. The pro-MMP-2 may form a complex with inhibitors such as TIMP (tissue inhibitor of metalloproteinase)-2 and TIMP-1, and the precursor of the present invention includes pro-MMP-2 present in the form of such complexes. The pro-MMP-2 may be present in any form, with no specific limitation.

The method for assaying (quantitative determination etc.) MMP-2 or the precursor in a sample is known, and in accordance with the present invention, MMP-2 or the precursor may be assayed (determined quantitatively) by known methods. For example, the method is carried out by assaying MMP-2 or the precursor in a system which is specific to MMP-2 or the precursor to determine the concentration of MMP-2 or the precursor as protein concentration or enzyme activity level. With no specific limitation, any method specific to MMP-2 or the precursor may be used for determining the concentration of MMP-2 or the precursor and the like, but the method, highly sensitive with good reproducibility, may be preferable.

More specifically, the method for determining protein concentration includes an immunological method by using an antibody with specificity to MMP-2 or the precursor. Additionally, the method for determining enzyme activity level includes a biochemical method by using a substrate at a high specificity to MMP-2.

According to the biochemical method for assaying enzyme activity, substrates at a high selectivity to MMP-2 include substrates hardly hydrolyzable with enzymes in samples, for example enzymes such as serine proteinase, peptidase, and esterase, except MMP-2, and readily hydrolyzable with MMP-2, and the substrates include for example gelatin, collagen or synthetic substrates with these characteristic structure portions, and the preferable substrates include (7-methoxycumarin-4-yl)acetyl-L-prolyl-L-leucyl-glycyl-L-leucyl-L-(N-(2,4-dinitrophenyl)-L-2,3- diaminopropionitryl)-L-alanyl-L-arginine amide (MCA) or N-acetyl-L-prolyl-L-leucyl-glycyl-L-leucyl-L-leucyl-glycine ethyl ester.

As to the method for assaying the enzyme activity of MMP-2, the hydrolysates of a substrate with MMP-2 may directly be assayed, or the enzyme activity may indirectly be assayed in combination with a system with potency to specifically assay any of the hydrolysates at a high sensitivity.

Assaying (quantitative determination etc.) of the MMP-2 precursor can be carried out by the method, by degrading the MMP-2 precursor by known methods (for example, treatment with trypsin or 4-aminophenyl mercury acetate (APMA)) to generate MMP-2 and assaying the enzyme activity of the generated MMP-2.

All the methods known as immunoassay methods may be used. General immunoassay methods using solid phases may be used, including sandwich assay, and competitive assay and binding inhibition assay. Specific methods include methods using assay systems wherein substrates are immobilized on solid carriers in place of antibodies, by using the binding potential between enzymes and substrates, or methods to directly detect the binding of MMP-2 or the precursor with immobilized antibodies by surface plasmon (SPR) with no use of labeled antibodies. These methods are more specifically disclosed in Japanese Patent Laid-open No. 60-2187, Japanese Patent Publication No. 7-34014, and Japanese Patent Laid-open Nos. 6-213888 and 7-159402. Additionally, methods using agglutination reaction or nepherometry using latex and blood cells or methods by western blotting may also be included. Any of these methods with difference in assay principle may be used for the assay. Generally, sandwich assay by means of antibodies immobilized on insoluble carriers and labeled antibodies is preferable.

Antibodies for use in immunoassay may satisfactorily be polyclonal antibodies or monoclonal antibodies. Any animal species may be satisfactory as the origins of the antibodies. When using two types of antibodies as in sandwich assay, a combination of an immobilized antibody and a labeled antibody to form a sandwich complex is satisfactory, even if the immobilized antibody and the labeled antibody are of the same antibody species or are of different antibody species. As the substance to label antibodies, radioactive substances, enzymes, fluorescent substances and biotin may be used.

According to the method for detecting chronic rejection in accordance with the present invention, the measured value of MMP-2 or the precursor (protein concentration or enzyme activity level or the like) per se or the increment thereof may directly be used for determining the presence of chronic rejection, but by calculating the ratio thereof to other markers to determine the relative value thereof, the relative value is used as an index of MMP-2 or the precursor for the determination. For urine as a sample, for example, a correction method on an urine creatine concentration basis (a method characterized by dividing the concentration of MMP-2 or the precursor by the creatine concentration in urine) is illustrated. For the practice of the methods of the present invention, preferably, a cut-off value is preset within a range such that at least 90% or more of patients with nearly normal organ functions after organtransplantation is judged as normal It is also possible to periodically assay $NO_3$ or MMP-2 or the precursor in patients with organ transplantation and determine the onset of chronic rejection on the basis of the measured value or the increment of the index.

In accordance with the present invention, as shown in the following examples, a method for detecting the presence or absence of bands due to the decomposition of substrates such as gelatin by electrophoresis on a polyacrylamide gel containing substrates such as gelatin may also be carried out, with no quantitation of MMP-2 or the precursor in samples.

The present invention will now be described more specifically with reference to the following examples, but the invention is not limited only to these examples.

EXAMPLE 1

In serum samples from patients with diagnosed by kidney biopsy as chronic rejection after kidney transplantation (A), patients with diagnosis of no onset of chronic rejection by kidney biopsy and the like whose renal functions were nearly normal (serum creatinine values of 1.2 mg/dl or less) (B) and normal subjects (C), the amount of $NO_3$ was assayed with an automatic analyzer of nitrate-form nitrogen and nitrite-form nitrogen (TCI-NOX1000, Tokyo Chemical Industry, Co.). Consequently, the serum $NO_3$ concentration in the patients with diagnosed chronic rejection after kidney transplantation was significantly higher than the serum $NO_3$ concentration in the patients with normal renal functions after kidney transplantation and the serum $NO_3$ concentration in the normal subjects, as shown in Table 1. It is shown that the amount of $NO_3$ in blood serves as an effective marker of chronic rejection.

TABLE 1

Serum $No_3$ concentrations ($\mu$M) in patients with kidney transplantation and normal subjects

| Samples | Number of Sample (n) | Mean ± Standard Deviation | (range) |
|---|---|---|---|
| Serum A (chronic rejection) | 15 | 238.2 ± 133.3* | (74.3–536.5) |
| Serum B (non-chronic rejection) | 24 | 35.8 ± 21.6 | (4.3–83.7) |
| Serum C (normal subject) | 7 | 31.6 ± 15.0 | (15.4–59.6) |

*$p < 0.01$; for the comparison with patients with non-chronic rejection or normal subjects (T-test)

EXAMPLE 2

(Zymogram; biochemical detection of MMP-2)

To an urine sample was added an equal volume of 0.5 M Tris buffer (pH 6.8) containing 8% SDS and 40% glycerol, followed by thorough mixing. After preparing 8% polyacrylamide gel containing 1 mg/ml gelatin, the resulting mixture was electrophoresed in it. After the electrophoresis, the gel was rinsed twice in 10 mM Tris buffer (pH 8.0) containing 2.5% Triton X-100 under shaking at ambient temperature for 30 minutes. Then, the buffer was replaced with 50 mM Tris buffer (pH 8.0) containing 0.5 mM calcium chloride and 10 $\mu$M zinc chloride, for incubation at 37° C. for 16 hours. The gel was stained with 1% Coomassie Blue R-250, 5% acetic acid, and 10% methanol for 30 minutes, followed by decoloring with 5% acetic acid and 10% methanol.

A transparent band was observed at the position of the gelatin decomposed by enzyme (MMP-2) on the blue background.

EXAMPLE 3

In urine samples from patients with the history of kidney transplantation back to one or more years ago and with diagnosed as chronic rejection based on the renal biopsy and serum creatinine values (2.0 mg/dl or more), and from patients within one year after kidney transplantation and with diagnosed by renal biopsy and the like as no onset of chronic rejection, whose renal functions were nearly normal (control group), MMP-2 activity was assayed according to the method of Example 2. Consequently, MMP-2 with a molecular weight of 70 kD was detected in 8 of 10 urine samples from the chronic rejection patients, but MMP-2 was detected in 1 of 14 urine samples from the control group.

This indicates that the increment of the MMP-2 concentration serves as an effective marker of chronic rejection

EXAMPLE 4

(Assaying of urine MMP-2 precursor concentration by immunoassay)

A serum MMP-2 assay kit with two types of monoclonal antibodies recognizing MMP-2 precursor molecule at different sites (for detecting pro-MMP-2 and a complex of pro-MMP-2 with TIMP-2 but not for detecting MMP-2) (manufactured by Fuji Pharmaceutical Industry, Co.) was used. Because urine pro-MMP-2 concentration is lower in urine than in serum, the conditions for the procedures in serum were modified for assaying the precursor in urine. More specifically, 150 µl of urine or a standard solution attached to the kit was placed in a test tube, followed by addition of 30 mM phosphate saline (pH 7.0) containing 1% bovine serum albumin and 10 mM EDTA and subsequent thorough mixing, and to the resulting mixture was added the antibody-bound bead for reaction at ambient temperature for 2 hours. The reaction solution was removed under aspiration with an aspirator, followed by addition of 300 µl of a labeled antibody solution attached to the kit, for reaction at ambient temperature for one hour. After the reaction solution was again removed under aspiration, the bead was transferred into another test tube, followed by addition of 300 µl of a coloring solution for reaction at ambient temperature for 30 minutes. By adding 1500 µl of a stop solution attached to the kit to the resulting reaction solution, the reaction was stopped. The absorbance of the reaction solution was measured at a wave length of 492 nm, while using distilled water as a control, and then, the pro-MMP-2 concentration in an urine sample was determined on the basis of a calibration curve prepared on the basis of the absorbance of the standard solution. Concurrently, urine creatinine concentration was assayed in a conventional manner, to calculate urine pro-MMP-2 concentration after correction on a creatinine basis.

EXAMPLE 5

Figure 2:
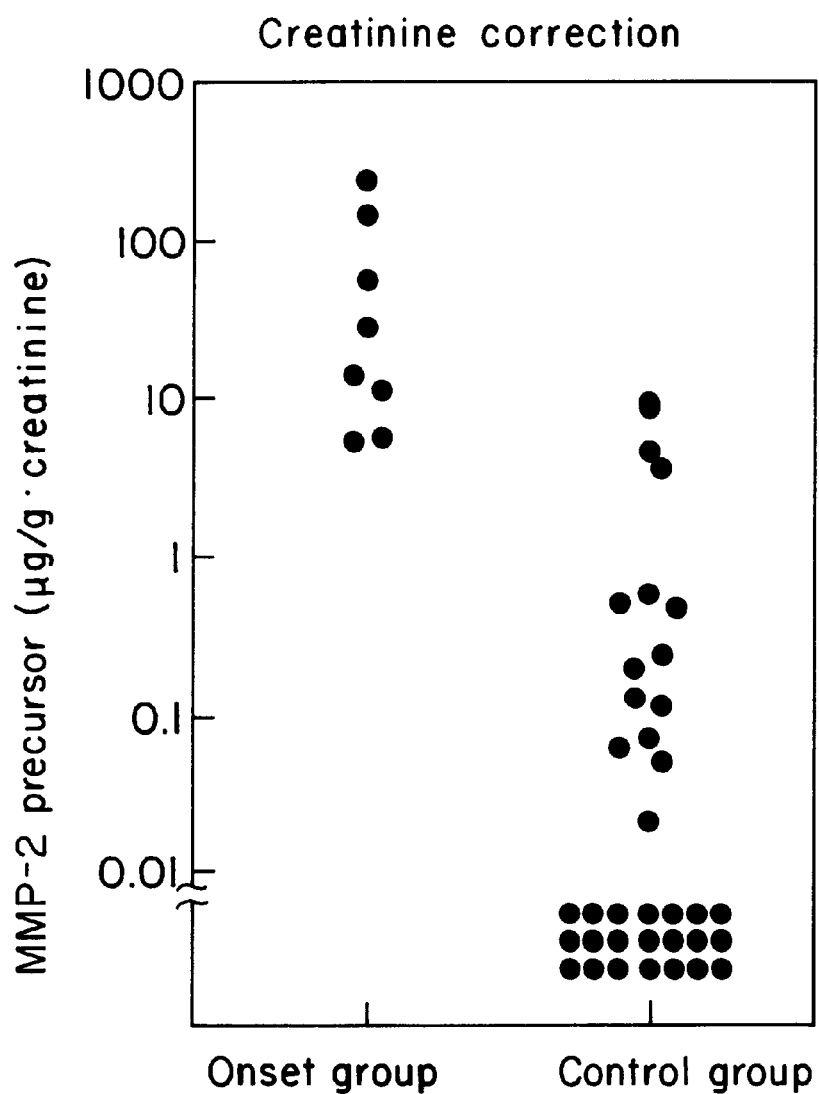
FIG. 2 depicts a histogram of urine MMP-2 precursor concentrations in patients with kidney transplantation after correction based on creatine concentrations.

In urine samples from 8 patients diagnosed as chronic rejection after kidney transplantation one or more years ago on the basis of kidney biopsy and the serum creatinine concentrations (onset group), and 36 patients within a year after kidney transplantation and with diagnosis of no onset of chronic rejection by kidney biopsy and the like, whose renal functions were nearly normal (with serum creatinine values of 1.5 mg/dl or less), (control group), the pro-MMP-2 concentration was assayed by the method in Example 4. Histograms with and without creatinine correction are shown in FIGS. 1 and 2. By presetting the cut-off value at 1 ng/ml in case of no creatinine correction, 92% of the control group was judged as negative, while 100% of the patients with diagnosed chronic rejection after kidney transplantation was judged as positive. By presetting the cut-off value at 5 µg/g creatinine in case of creatinine correction, 95% of the control group was judged as negative, while 100% of the patients with diagnosed chronic rejection after kidney transplantation was judged as positive. By presetting the cut-off value at 1 µg/g·creatinine, 89% of the control group was still judged as negative.

EXAMPLE 6

In urine samples from 2 patients with kidney transplantation before the onset of chronic rejection due to kidney transplantation and after the onset thereof, the pro-MMP-2 concentration (creatinine-corrected value) was assayed according to the method in Example 4. The results are shown in Table 2. The pro-MMP-2 concentration was greatly increased after the onset, which indicates that the elevation of the pro-MMP-2 concentration is effective in determining the onset of chronic rejection due to kidney transplantation.

TABLE 2

|  | Before onset (µ g/g · creatinine) | After onset (µ g/g · creatinine) |
| --- | --- | --- |
| Patient 1 | 1.3 | 14.6 |
| Patient 2 | 0.6 | 29.4 |

INDUSTRIAL APPLICABILITY

By practicing the method of the present invention, the increase of the concentration of $NO_3$, MMP-2 or the precursor in body fluids (samples), such as serum and urine, can enable the detection of chronic rejection at its early stage.

What is claimed is:

1. A method for detecting chronic rejection after organ transplantation, comprising presetting a cut-off value of the concentration of the matrix metalloproteinase (MMP)-2 or the precursor thereof for determining the presence or absence of chronic rejection after organ transplantation within a range such that at least 90% or more of patients with nearly normal organ functions after organ transplantation are judged as normal and detecting matrix metalloproteinase (MMP)-2 or the precursor thereof in urine or blood of patients with organ transplantation.

2. A method according to claim 1, comprising detecting MMP-2 or the precursor thereof in a urine sample.

3. A method according to claim 1, wherein the organ transplantation is kidney transplantation.

4. A method according to claim 2, comprising presetting a cut-off value for determining the presence or absence of chronic rejection after kidney transplantation within a range of 0.1 to 10.0 ng/ml as the concentration of the MMP-2 precursor in a urine sample.

5. A method according to claim 4, characterized by presetting the cut-off value within a range of 0.5 to 5.0 ng/ml.

6. A method according to claim 2, comprising assaying the MMP-2 precursor concentration and creatinine concentration in a urine sample, and presetting a cut-off value of an index obtained by dividing the concentration of MMP-2 or the precursor by the creatinine concentration in urine for determining the presence or absence of chronic rejection after kidney transplantation within a range of 0.1 to 20.0 µg/g creatinine.

7. A method according to claim 6, characterized by presetting the cut-off value within a range of 0.5 to 10.0 µg/g·creatinine.

8. A method according to any one of claims 1 or 3, wherein the detecting is carried out by immunoassay.

9. A method according to claim 8, wherein the immunoassay is enzyme immunoassay.

10. A method according to claim 9, wherein the enzyme immunoassay is a sandwich assay.

11. A method according to claim 8, wherein the immunoassay is a sandwich assay.

* * * * *